US008105325B2

(12) United States Patent
Suslov

(10) Patent No.: US 8,105,325 B2
(45) Date of Patent: Jan. 31, 2012

(54) PLASMA-GENERATING DEVICE, PLASMA SURGICAL DEVICE, USE OF A PLASMA-GENERATING DEVICE AND METHOD OF GENERATING A PLASMA

(75) Inventor: Nikolay Suslov, Västra Frölunda (SE)

(73) Assignee: Plasma Surgical Investments Limited, Tortula (VG)

(*) Notice: Subject to any disclaimer, the term of this patent is extended or adjusted under 35 U.S.C. 154(b) by 1498 days.

(21) Appl. No.: 11/482,582

(22) Filed: Jul. 7, 2006

(65) Prior Publication Data

US 2007/0021748 A1 Jan. 25, 2007

(30) Foreign Application Priority Data

Jul. 8, 2005 (SE) ...................................... 0501602

(51) Int. Cl.
*A61B 18/14* (2006.01)
(52) U.S. Cl. ........................................... 606/45; 606/39
(58) Field of Classification Search .................... 606/40, 606/45, 49; 315/111.21, 111.01
See application file for complete search history.

(56) References Cited

U.S. PATENT DOCUMENTS

| | | | |
|---|---|---|---|
| 3,077,108 | A | 2/1963 | Gage et al. |
| 3,082,314 | A | 3/1963 | Yoshiaki Arata et al. |
| 3,100,489 | A | 8/1963 | Bagley |
| 3,145,287 | A | 8/1964 | Seibein et al. |
| 3,153,133 | A | 10/1964 | Ducati |
| 3,270,745 | A | 9/1966 | Wood |
| 3,360,988 | A | 1/1968 | Stein et al. |
| 3,413,509 | A | 11/1968 | Cann et al. |

(Continued)

FOREIGN PATENT DOCUMENTS

AU 2000250426 6/2005

(Continued)

OTHER PUBLICATIONS

Asawanonda et al., 2000, "308-nm excimer laser for the treatment of psoriasis: a dose-response study."Arach. Dermatol. 136:619-24.

(Continued)

*Primary Examiner* — Linda Dvorak
*Assistant Examiner* — Jaymi Della
(74) *Attorney, Agent, or Firm* — Jones Day

(57) ABSTRACT

The present invention relates to a plasma-generating device comprising an anode, a cathode and an elongate plasma channel which extends substantially in the direction from said cathode to said anode. The plasma channel has a throttling portion which is arranged in said plasma channel between said cathode and an outlet opening arranged in said anode. Said throttling portion divides said plasma channel into a high pressure chamber, which is positioned on a side of the throttling portion closest to the cathode, and has a first maximum cross-sectional surface transversely to the longitudinal direction of the plasma channel, and a low pressure chamber, which opens into said anode and has a second maximum cross-sectional surface transversely to the longitudinal direction of the plasma channel, said throttling portion having a third cross-sectional surface transversely to the longitudinal direction of the plasma channel which is smaller than said first maximum cross-sectional surface and said second maximum cross-sectional surface. Moreover at least one intermediate electrode is arranged between said cathode and said throttling portion. The invention also relates to a plasma surgical device, use of such a plasma surgical device in surgery and a method of generating a plasma.

25 Claims, 4 Drawing Sheets

U.S. PATENT DOCUMENTS

| | | | |
|---|---|---|---|
| 3,433,991 | A | 3/1969 | Whyman |
| 3,434,476 | A | 3/1969 | Shaw et al. |
| 3,534,388 | A | 10/1970 | Osamu et al. |
| 3,628,079 | A | 12/1971 | Dobbs et al. |
| 3,676,638 | A | 7/1972 | Stand |
| 3,775,825 | A | 12/1973 | Wood et al. |
| 3,803,380 | A | 4/1974 | Ragaller |
| 3,838,242 | A | 9/1974 | Goucher |
| 3,851,140 | A | 11/1974 | Coucher |
| 3,866,089 | A * | 2/1975 | Hengartner .............. 315/111.21 |
| 3,903,891 | A | 9/1975 | Brayshaw |
| 3,914,573 | A | 10/1975 | Muehlberger |
| 3,938,525 | A | 2/1976 | Coucher |
| 3,991,764 | A | 11/1976 | Incropera et al. |
| 3,995,138 | A | 11/1976 | Kalev et al. |
| 4,029,930 | A | 6/1977 | Sagara et al. |
| 4,035,684 | A | 7/1977 | Svoboda et al. |
| 4,041,952 | A | 8/1977 | Morrison, Jr. et al. |
| 4,201,314 | A | 5/1980 | Samuels et al. |
| 4,256,779 | A | 3/1981 | Sokol et al. |
| 4,317,984 | A | 3/1982 | Fridlyand |
| 4,397,312 | A | 8/1983 | Molko |
| 4,445,021 | A | 4/1984 | Irons et al. |
| 4,661,682 | A | 4/1987 | Gruner et al. |
| 4,672,163 | A | 6/1987 | Matsui et al. |
| 4,674,683 | A | 6/1987 | Fabel |
| 4,682,598 | A | 7/1987 | Beraha |
| 4,696,855 | A | 9/1987 | Pettit, Jr. et al. |
| 4,711,627 | A | 12/1987 | Oeschsle et al. |
| 4,713,170 | A | 12/1987 | Saibic |
| 4,743,734 | A | 5/1988 | Garlanov et al. |
| 4,764,656 | A | 8/1988 | Browning |
| 4,777,949 | A | 10/1988 | Perlin |
| 4,780,591 | A | 10/1988 | Bernecki et al. |
| 4,781,175 | A | 11/1988 | McGreevy et al. |
| 4,784,321 | A | 11/1988 | Delaplace |
| 4,785,220 | A | 11/1988 | Brown et al. |
| 4,839,492 | A | 6/1989 | Bouchier et al. |
| 4,841,114 | A | 6/1989 | Browning |
| 4,853,515 | A | 8/1989 | Willen et al. |
| 4,855,563 | A | 8/1989 | Beresnev et al. |
| 4,866,240 | A | 9/1989 | Webber |
| 4,869,936 | A | 9/1989 | Moskowitz et al. |
| 4,874,988 | A | 10/1989 | English |
| 4,877,937 | A | 10/1989 | Muller |
| 4,916,273 | A | 4/1990 | Browning |
| 4,924,059 | A | 5/1990 | Rotolico et al. |
| 5,008,511 | A | 4/1991 | Ross |
| 5,013,883 | A | 5/1991 | Fuimefreddo et al. |
| 5,100,402 | A | 3/1992 | Fan |
| 5,144,110 | A | 9/1992 | Marantz et al. |
| 5,151,102 | A | 9/1992 | Kamiyama et al. |
| 5,201,900 | A | 4/1993 | Nardella |
| 5,207,691 | A | 5/1993 | Nardella |
| 5,211,646 | A | 5/1993 | Alperovich et al. |
| 5,217,460 | A | 6/1993 | Knoepfler |
| 5,225,652 | A | 7/1993 | Landes |
| 5,227,603 | A | 7/1993 | Doolette et al. |
| 5,261,905 | A | 11/1993 | Doresey |
| 5,285,967 | A | 2/1994 | Weidman |
| 5,332,885 | A | 7/1994 | Landes |
| 5,352,219 | A | 10/1994 | Reddy |
| 5,396,882 | A | 3/1995 | Zapol |
| 5,403,312 | A | 4/1995 | Yates et al. |
| 5,406,046 | A | 4/1995 | Landes |
| 5,408,066 | A | 4/1995 | Trapani et al. |
| 5,412,173 | A | 5/1995 | Muehlberger |
| 5,445,638 | A | 8/1995 | Rydell et al. |
| 5,452,854 | A | 9/1995 | Keller |
| 5,460,629 | A | 10/1995 | Shlain et al. |
| 5,485,721 | A | 1/1996 | Steenborg |
| 5,514,848 | A | 5/1996 | Ross et al. |
| 5,519,183 | A | 5/1996 | Mueller |
| 5,527,313 | A | 6/1996 | Scott et al. |
| 5,573,682 | A | 11/1996 | Beason, Jr. et al. |
| 5,582,611 | A | 12/1996 | Tsuruta et al. |
| 5,620,616 | A | 4/1997 | Anderson et al. |
| 5,629,585 | A | 5/1997 | Altmann |
| 5,637,242 | A | 6/1997 | Muehlberger |
| 5,640,843 | A | 6/1997 | Aston |
| 5,662,680 | A | 9/1997 | Desai |
| 5,665,085 | A | 9/1997 | Nardella |
| 5,679,167 | A | 10/1997 | Muehlberger |
| 5,680,014 | A | 10/1997 | Miyamoto et al. |
| 5,688,270 | A | 11/1997 | Yates et al. |
| 5,697,281 | A | 12/1997 | Eggers et al. |
| 5,702,390 | A | 12/1997 | Austin et al. |
| 5,720,745 | A | 2/1998 | Farin et al. |
| 5,733,662 | A | 3/1998 | Bogachek |
| 5,797,941 | A | 8/1998 | Schulze et al. |
| 5,827,271 | A | 10/1998 | Buysse et al. |
| 5,833,690 | A | 11/1998 | Yates et al. |
| 5,837,959 | A | 11/1998 | Muehlberger et al. |
| 5,843,079 | A | 12/1998 | Suslov |
| 5,858,469 | A | 1/1999 | Sahoo et al. |
| 5,858,470 | A | 1/1999 | Bernecki et al. |
| 5,897,059 | A | 4/1999 | Muller |
| 5,932,293 | A | 8/1999 | Belashchenko et al. |
| 6,003,788 | A | 12/1999 | Sedov |
| 6,042,019 | A | 3/2000 | Rusch |
| 6,099,523 | A | 8/2000 | Kim et al. |
| 6,114,649 | A | 9/2000 | Delcea |
| 6,135,998 | A | 10/2000 | Palanker |
| 6,137,078 | A | 10/2000 | Keller |
| 6,137,231 | A | 10/2000 | Anders |
| 6,162,220 | A | 12/2000 | Nezhat |
| 6,169,370 | B1 * | 1/2001 | Platzer ..................... 315/111.21 |
| 6,181,053 | B1 | 1/2001 | Roberts |
| 6,202,939 | B1 | 3/2001 | Delcea |
| 6,273,789 | B1 | 8/2001 | LaSalle et al. |
| 6,283,386 | B1 | 9/2001 | Van Steenkiste et al. |
| 6,352,533 | B1 | 3/2002 | Ellman et al. |
| 6,386,140 | B1 | 5/2002 | Muller et al. |
| 6,392,189 | B1 | 5/2002 | Delcea |
| 6,443,948 | B1 | 9/2002 | Suslov et al. |
| 6,475,215 | B1 | 11/2002 | Tanrisever |
| 6,514,252 | B2 | 2/2003 | Nezhat et al. |
| 6,515,252 | B1 | 2/2003 | Girold |
| 6,528,947 | B1 | 3/2003 | Chen et al. |
| 6,548,817 | B1 | 4/2003 | Anders |
| 6,562,037 | B2 | 5/2003 | Paton et al. |
| 6,629,974 | B2 | 10/2003 | Penny et al. |
| 6,657,152 | B2 | 12/2003 | Shimazu |
| 6,669,106 | B2 | 12/2003 | Delcea |
| 6,676,655 | B2 | 1/2004 | McDaniel et al. |
| 6,780,184 | B2 | 8/2004 | Tanrisever |
| 6,845,929 | B2 | 1/2005 | Dolatabadi et al. |
| 6,886,757 | B2 | 5/2005 | Byrnes et al. |
| 6,958,063 | B1 | 10/2005 | Soll et al. |
| 6,972,138 | B2 | 12/2005 | Heinrich et al. |
| 6,986,471 | B1 | 1/2006 | Kowalsky et al. |
| 7,025,764 | B2 | 4/2006 | Paton et al. |
| 7,030,336 | B1 | 4/2006 | Hawley |
| 7,118,570 | B2 | 10/2006 | Tetzlaff et al. |
| 7,589,473 | B2 | 9/2009 | Suslov |
| 2001/0041227 | A1 | 11/2001 | Hislop |
| 2002/0013583 | A1 | 1/2002 | Camran et al. |
| 2002/0071906 | A1 | 6/2002 | Rusch |
| 2002/0091385 | A1 | 7/2002 | Paton et al. |
| 2002/0097767 | A1 | 7/2002 | Krasnov |
| 2003/0030014 | A1 | 2/2003 | Wieland et al. |
| 2003/0040744 | A1 | 2/2003 | Latterell et al. |
| 2003/0075618 | A1 | 4/2003 | Shimazu |
| 2003/0114845 | A1 | 6/2003 | Paton et al. |
| 2003/0125728 | A1 | 7/2003 | Nezhat et al. |
| 2003/0178511 | A1 | 9/2003 | Dolatabadi et al. |
| 2003/0190414 | A1 | 10/2003 | Van Steenkiste |
| 2004/0018317 | A1 | 1/2004 | Heinrich et al. |
| 2004/0064139 | A1 | 4/2004 | Yossepowitch |
| 2004/0068304 | A1 | 4/2004 | Paton et al. |
| 2004/0116918 | A1 | 6/2004 | Konesky |
| 2004/0124256 | A1 | 7/2004 | Itsukaichi et al. |
| 2004/0129222 | A1 | 7/2004 | Nylen et al. |
| 2004/0195219 | A1 | 10/2004 | Conway |
| 2005/0082395 | A1 | 4/2005 | Gardega |
| 2005/0120957 | A1 | 6/2005 | Kowalsky et al. |
| 2005/0192610 | A1 | 9/2005 | Houser et al. |

| | | | |
|---|---|---|---|
| 2005/0192611 | A1 | 9/2005 | Houser |
| 2005/0192612 | A1 | 9/2005 | Houser et al. |
| 2005/0234447 | A1 | 10/2005 | Paton et al. |
| 2005/0255419 | A1 | 11/2005 | Belashchenko et al. |
| 2006/0004354 | A1 | 1/2006 | Suslov |
| 2006/0037533 | A1 | 2/2006 | Belashchenko et al. |
| 2006/0049149 | A1 | 3/2006 | Shimazu |
| 2006/0090699 | A1 | 5/2006 | Muller |
| 2006/0091116 | A1 | 5/2006 | Suslov |
| 2006/0091117 | A1 | 5/2006 | Blankenship et al. |
| 2006/0091119 | A1 | 5/2006 | Zajchowski et al. |
| 2006/0108332 | A1 | 5/2006 | Belashchenko |
| 2006/0217706 | A1 | 9/2006 | Lau et al. |
| 2006/0287651 | A1 | 12/2006 | Bayat |
| 2007/0021747 | A1 | 1/2007 | Suslov |
| 2007/0021748 | A1 | 1/2007 | Suslov |
| 2007/0029292 | A1 | 2/2007 | Suslov |
| 2007/0038214 | A1 | 2/2007 | Morley et al. |
| 2007/0138147 | A1 | 6/2007 | Molz et al. |
| 2007/0173871 | A1 | 7/2007 | Houser et al. |
| 2007/0173872 | A1 | 7/2007 | Neuenfeldt |
| 2007/0191828 | A1 | 8/2007 | Houser et al. |
| 2008/0015566 | A1 | 1/2008 | Livneh |
| 2008/0071206 | A1 | 3/2008 | Peters |
| 2008/0114352 | A1 | 5/2008 | Long et al. |
| 2008/0185366 | A1 | 8/2008 | Suslov |
| 2009/0039789 | A1 | 2/2009 | Nikolay |
| 2009/0039790 | A1 | 2/2009 | Suslov |

FOREIGN PATENT DOCUMENTS

| | | | |
|---|---|---|---|
| AU | 2006252145 | | 1/2007 |
| CA | 983586 | * | 2/1976 |
| CA | 1 144 104 | | 4/1983 |
| CA | 1308722 | | 10/1992 |
| CA | 2594515 | | 7/2006 |
| CN | 1331836 | A | 1/2002 |
| CN | 1557731 | | 12/2004 |
| DE | 2033072 | | 2/1971 |
| DE | 10127261 | | 9/1993 |
| DE | 4209005 | | 12/2002 |
| EP | 0411170 | | 2/1991 |
| EP | 0 748 149 | | 12/1996 |
| EP | 0851040 | | 7/1998 |
| EP | 1293169 | | 3/2003 |
| EP | 1570798 | | 9/2005 |
| ES | 2026344 | | 4/1992 |
| FR | 2 193 299 | | 2/1974 |
| FR | 2 567 747 | | 1/1986 |
| FR | 2567747 | | 1/1986 |
| GB | 751735 | | 7/1956 |
| GB | 921016 | | 3/1963 |
| GB | 1 125 806 | | 9/1968 |
| GB | 1 176 333 | | 1/1970 |
| GB | 1 268 843 | | 3/1972 |
| GB | 1268843 | | 3/1972 |
| GB | 2407050 | | 4/2005 |
| JP | 47009252 | | 3/1972 |
| JP | 54120545 | | 2/1979 |
| JP | 57001580 | | 1/1982 |
| JP | 57068269 | | 4/1982 |
| JP | 62123004 | | 6/1987 |
| JP | 1198539 | | 8/1989 |
| JP | 3 043 678 | | 2/1991 |
| JP | 06262367 | | 9/1994 |
| JP | 9299380 | | 11/1997 |
| JP | 10024050 | | 1/1998 |
| JP | 10234744 | | 9/1998 |
| JP | 2002541902 | | 12/2002 |
| JP | 2005539143 | | 12/2005 |
| JP | 2008036001 | | 2/2008 |
| MX | PA04010281 | | 6/2005 |
| RU | 2178684 | | 1/2002 |
| RU | 2183480 | | 6/2002 |
| RU | 2183946 | | 6/2002 |
| WO | WO9219166 | | 11/1992 |
| WO | WO 96/06572 | | 3/1996 |
| WO | WO9711647 | | 4/1997 |
| WO | WO0162169 | | 8/2001 |
| WO | WO0230308 | | 4/2002 |
| WO | WO 03/028805 | | 4/2003 |
| WO | WO 2004/028221 | | 4/2004 |
| WO | WO 2004/030551 | | 4/2004 |
| WO | WO 2004/105450 | | 12/2004 |
| WO | WO 2005/09595 | | 10/2005 |
| WO | WO 2005/099595 | | 10/2005 |
| WO | WO2005009959 | | 10/2005 |
| WO | WO 2006/012165 | | 2/2006 |
| WO | WO 2007/003157 | | 1/2007 |
| WO | WO 2007/006516 | | 1/2007 |
| WO | WO 2007/006517 | | 1/2007 |
| WO | WO 2007/040702 | | 4/2007 |

OTHER PUBLICATIONS

Coven et al., 1999, "PUVA-induced lymphocyte apoptosis: mechanism of action in psoriasis." Photodermatol. Photoimmunol. Photomed. 15:22-7.

Dabringhausen et al., 2002, "Determination of HID electrode falls in a model lamp I: Pyrometric measurements." J. Phys. D. Appl. Phys. 35:1621-1630.

Feldman et al., 2002, "Efficacy of the 308-nm excimer laser for treatment of psoriasis: results of a multicenter study." J. Am Acad. Dermatol. 46:900-6.

Gerber et al., 2003, "Ultraviolet B 308-nm excimer laser treatment of psoriasis: a new phototherapeutic approach." Br. J. Dermatol. 149:1250-8.

Honigsmann, 2001, "Phototherapy for psoriasis." Clin. Exp. Dermatol. 26:343-50.

Lichtenberg et al., 2002, "Observation of different modes of cathodic arc attachment to HID electrodes in a model lamp." J. Phys. D. Appl. Phys. 35:1648-1656.

PCT International Search Report, dated Oct. 23, 2007, International App. No. PCT/EP2007/000919.

PCT Written Opinion of the International Searching Authority dated Oct. 23, 2007, International App. No. PCT/EP2007/000919.

Schmitz & Riemann, 2002, "Analysis of the cathode region of atmospheric pressure discharges." J. Phys. D. Appl. Phys. 35:1727-1735.

Trehan & Taylor, 2002, "Medium-dose 308-nm excimer laser for the treatment of psoriasis." J. Am. Acad. Dermatol. 47:701-8.

Video—Tumor Destruction Using Plasma Surgery, by Douglas A. Levine, M.D.

Video—Laparoscopic Management of Pelvic Endometriosis, by Ceana Nezhat, M.D.

Video—Tissue Coagulation, by Denis F. Branson, M.D.

Office Action of U.S. Appl. No. 11/701,911, dated Sep. 29, 2009.

Plasma Surgical Headlines Article: Atlanta, Feb. 2, 2010—"New Facilities Open in UK and US".

Plasma Surgical Headlines Article: Atlanta, Feb. 2, 2010—"PlasmaJet to be Featured in Live Case at Endometriosis 2010 in Milan, Italy".

Plasma Surgical Headlines Article: Chicago, Sep. 17, 2008—"PlasmaJet Named Innovation of the Year by the Society of a Laparoendoscopic Surgeons".

Marino, M.D., "A new option for patients facing liver resection surgery", Thomas Jefferson University Hospital.

Branson, M.D., 2005, "Preliminary experience with neutral plasma, a new coagulation technology, in plastic surgery", Fayetteville, NY.

Merloz, 2007, "Clinical evaluation of the Plasma Surgical PlasmaJet tissue sealing system in orthopedic surgery—Early report", Orthopedic Surgery Department, University Hospital, Grenoble, France.

Charpentier et al., 2008, "Multicentric medical registry on the use of the Plasma Surgical PlasmaJet System in thoracic surgery", Club Thorax.

Iannelli et al., 2005, "Neutral plasma coagulation (NPC)—A preliminary report on a new technique for post-bariatric corrective abdominoplasty", Department of Digestive Surgery, University Hospital, Nice, France.

Gugenheim et al., 2006, "Open, muliticentric, clinical evaluation of the technical efficacy, reliability, safety, and clinical tolerance of the plasma surgical PlasmaJet System for intra-operative coagulation in open and laparoscopic general surgery", Department of Digestive Surgery, University Hospital, Nice, France.

Sonoda et al., "Pathologic analysis of ex-vivo plasma energy tumor destruction in patients with ovarian or peritoneal cancer", Gynecology Service, Department of Surgery—Memorial Sloan-Kettering Cancer Center, New York, NY—Poster.
White Paper —Plasma Technology and its Clinical Application: An introduction to Plasma Surgery and the PlasmaJet—a new surgical tehnology.
White Paper—A Tissue Study using the Plasmalet for coagulation: A tissue study comparing the PlasmaJet with argon enhanced electrosurgery and fluid coupled clectrosurgery.
PlasmaJet English Brochure.
Plasma Surgery: A Patient Safety Solution (Study Guide 002).
News Release and Video—2009, New Sugical Technology Offers Better Outcomes for Women's Reproductive Disorders: Stanford First in Bay Area to Offer PlasmaJet, Stanford Hospital and Clinics.
www.plasmasurgical.com, as of Feb. 18, 2010.
510(k) Summary, dated Oct. 30, 2003.
510(k) Summary, dated Jun. 2, 2008.
International Preliminary Report on Patentability of International application No. PCT/EP2007/006939, dated Feb. 9, 2010.
International Preliminary Report on Patentability of International application No. PCT/EP2007/006940, dated Feb. 9, 2010.
U.S. Appl. No. 12/696,411; Suslov, Jan. 29, 2010.
U.S. Appl. No. 12/557,645; Suslov, Sep. 11, 2009.
510(k) Notification (21 CFR 807.90(e)) for the Plasma Surgical Ltd. PlasmaJet® Neutral Plasma Surgery System, Section 10—Executive Summary—K080197.
Aptekman, 2007, "Spectroscopic analysis of the PlasmaJet argon plasma with 5mm-0.5 coag-cut handpieces", Document PSSRP-106—K080197.
Chen et al., 2006, "What do we know about long laminar plasma jets?", Pure Appl Chem; 78(6):1253-1264.
Cheng et al., 2006, "Comparison of laminar and turbulent thermal plasma jet characteristics—a modeling study", Plasma Chem Plasma Process; 26:211-235.
CoagSafe™ Neutral Plasma Coagulator Operator Manual, Part No. OMC-2100-1, Revision 1.1, dated Mar. 2003—Appendix 1ofK030819.
Deb et al., "Histological quantification issue damage caused in vivo by neutral PlasmaJet coagulator", Nottingham University Hospitals, Queen's medical Centre, Nottingham NG7 2UH—Poster.
Electrosurgical Generators Force FX™ Electrosurgical Generators by ValleyLab—K080197.
ERBE APC 300 Argon Plasma Coagulation Unit for Endoscopic Applications, Brochure—Appendix 4 of K030819.
FORCE Argon™ II System, Improved precision and control in electrosurgery, by Valleylab—K080197.
Haines et al., "Argon neutral plasma energy for laparoscopy and open surgery recommended power settings and applications", Royal Surrey County Hospital, Guildford Surrey, UK.
Haemmerich et al., 2003, "Hepatic radiofrequency ablation with internally cooled probes: effect of coolant temperature on lesion size", IEEE Transactions of Biomedical Engineering; 50(4):493-500.
Huang et al., 2008, "Laminar/turbulent plasma jets generated at reduced pressure", IEEE Transaction on Plasma Science; 36(4): 1052-1053.
Letter to FDA re: 501(k) Notification (21 CFR 807.90(e)) for the PlasmJet® Neutral Plasma Surgery System, dated Jun. 2, 2008—K080197.
McClurken et al., "Histologic characteristics of the TissueLink Floating Ball device coagulation on porcine liver", TissueLink Medical, Inc., Dover, NH; Pre-Clinical Study #204.
McClurken et al., "Collagen shrinkage and vessel sealing", TissueLink Medical, Inc., Dover, NH; Technical Brief #300.
Nezhat et al., 2009, "Use of neutral argon plasma in the laparoscopic treatment of endometriosis", Journal of the Society of Laparoendoscopic Surgeons.
Notice of Allowance dated May 15, 2009, of U.S. Appl. No. 11/890,938.
Palanker et al., 2008, "Electrosurgery with cellular precision", IEEE Transactions of Biomedical Engineering; 55(2):838-841.
Pan et al., 2001, "Generation of long, laminar plasma jets at atmospheric pressure and effects of low turbulence", Plasma Chem Plasma Process; 21(1):23-35.
Pan et al., 2002, "Characteristics of argon laminar DC Plasma Jet at atmospheric pressure", Plasma Chem and Plasma Proc; 22(2):271-283.
PlasmaJet Neutral Plasma Coagulator Operator Manual, Part No. OMC-2100-1 (Revision 1.7. dated May 2004)—K030819.
Plasmajet Neutral Plasma Coagulator Brochure mpb 2100—K080197.
Plasmajet Operator Manual Part No. OMC-2130-EN (Revision 3.1/ Draft) dated May 2008—K080197.
Premarket Notification 510(k) Submission, Plasma Surgical Ltd.—PlasmaJet™ (formerly CoagSafe™) Neutral Plasma Coagulator, Additional information provided in response to the e-mail request dated Jul. 14, 2004—K0308I9.
Premarket Notification 510(k) Submission, Plasma Surgical Ltd. CoagSafe™, Section 4 Device Description—K030819.
Premarket Notification 510(k) Submission,Plasma Surgical Ltd. PlasmaJet®, Section I I Device Description—K080197.
Premarket Notification 510(k) Submission, Plasma Surgical Ltd. CoagSafe™, Section 5 Substantial Equivalence—K030819.
Report on the comparative analysis of morphological changes in tissue from different organs after using the PlasmaJet version 3 (including cutting handpieces), Aug. 2007—K080197.
Severtsev et al., "Comparison of different equipment for final haemostasis of the wound surface of the liver following resection", Dept. of Surgery, Postgraduate and Research Centre, Medical Centre of the Directorate of Presidential Affairs of the Russian Federation, Moscow, Russia—K030819.
The Edge in Electrosurgery From Birtcher, Brochure—Appendix 4 of K030819.
The Valleylab FORCE GSU System, Brochure—Appendix 4 of K030819.
Treat, "A new thermal device for sealing and dividing blood vessels", Dept. of Surgery, Columbia University, New York, NY.
Zenker, 2008, "Argon plasma coagulation", German Medical Science; 3(1):1-5.
Device drawings submitted pursuant to MPEP §724.
PCT International Search Report, dated Jan. 16, 2007, International App. No. PCT/EP2006/006688.
International-type Search Report, dated Jan. 18, 2006, Swedish App. No. 0501602-7.
Office Action dated Oct. 18, 2007 of U.S. Appl. No. 11/701,911.
Office Action dated Feb. 1, 2008 of U.S. Appl. No. 11/482,580.
Office Action dated Apr. 17, 2008 of U.S. Appl. No. 11/701,911.
PCT International Search Report PCT/EP2007/006939, dated May 26, 2008.
PCT Invitation to Pay Additional Fees PCT/EP2007/006940, dated May 20, 2008.
PCT Written Opinion of the International Searching Authority PCT/ EP2007/006939, dated May 26, 2008.
Davis J.R. (ed) ASM Thermal Spray Society, Handbook of Thermal Spray Technology, 2004, U.S. 42-168.
PCT Written Opionin of the International Searching Authority dated Feb. 14, 2007, International App. No. PCT/EP2006/006688.
PCT International Search Report dated Feb. 22, 2007, International App. No. PCT/EP2006/006689.
PCT Written Opionin of the International Searching Authority dated Feb. 22, 2007, International App. No. PCT/EP2006/006689.
PCT International Search Report dated Feb. 22, 2007, International App. No. PCT/EP2006/006690.
PCT Written Opionin of the International Searching Authority dated, dated Feb. 22, 2007, International App. No. PCT/EP2006/006690.
International-type Search report dated Jan. 18, 2006, Swedish App. No. 0501604-3.
International-type Search report dated Jan. 18, 2006, Swedish App. No. 0501603-5.
PCT Written Opinion of the International Searching Authority PCT/ EP2007/006940.
PCT International Search Report PCT/EP2007/006940.

PCT International Preliminary Report on Patentability and Written Opinion of the International Searching Authority, dated Aug. 4, 2009, International App. No. PCT/EP2007/000919.
Office Action of U.S. Appl. No. 11/890,937, dated Sep. 17, 2009.
Office Action of U.S. Appl. No. 11/482,583, dated Oct. 18, 2009.
U.S. Appl. No. 12/841,361, filed Jul. 22, 2010, Suslov.
International Search Report of International application No. PCT/EP2010/051130, dated Sep. 27, 2010.
Written Opinion of International application No. PCT/EP2010/051130, dated Sep. 27, 2010.
Severtsev et al. 1997, "Polycystic liver disease: sclerotherapy, surgery and sealing of cysts with fibrin sealant", European Congress of the International Hepatobiliary Association, Hamburg, Germany Jun. 8-12; p. 259-263.
Severtsev et al., "Comparison of different equipment for final haemostasis of the wound surface of the liver following resection", Dept. of Surgery, Postgraduate and Research Centre, Medical Centre of the Directorate of Presidential Affairs of the Russian Federation, Moscow, Russia—K030819.
European Office Action of application No. 07786583.0/1226, dated Jun. 29, 2010.
Office Action of U.S. Appl. No. 11/701,911 dated Apr. 2, 2010.
Office Action of U.S. Appl. No. 11/890,937 dated Apr. 9, 2010.
Office Action of U.S. Appl. No. 11/482,581, dated Jun. 24, 2010.
Office Action of U.S. Appl. No. 11/701,911 dated Jul. 19, 2010.
Office Action of U.S. Appl. No. 12/557,645, dated Nov. 26, 2010.
Office Action of U.S. Appl. No. 11/482,581, dated Dec. 8, 2010.
Notice of Allowance of U.S. Appl. No. 11/701,911, dated Dec. 6, 2010.
International Search Report of application No. PCT/EP2010/060641, dated Apr. 14, 2011.
Written Opinion of International application No. PCT/EP2010/060641, dated Apr. 14, 2011.
Chinese Office Action (translation) of application No. 200680030225.5, dated Jun. 11, 2010.
Chinese Office Action (translation) of application No. 200680030216.6, dated Oct. 26, 2010.
Chinese Office Action (translation) of application No. 200680030194.3, dated Jan. 31, 2011.
Chinese Office Action (translation) of application No. 200680030225.5, dated Mar. 9, 2011.
Japanese Office Action (translation) of application No. 2008-519873, dated Jun. 10, 2011.
Notice of Allowance of U.S. Appl. No. 12/557,645, dated May 26, 2011.
Office Action dated Mar. 13, 2009 of U.S. Appl. No. 11/701,911.
Office Action dated Mar. 19, 2009 of U.S. Appl. No. 11/482,580.
Notice of Allowance and Fees Due of U.S. Appl. No. 11/482,581, Oct. 28, 2011.
Chinese Office Action of application No. 2007801008583, dated Oct. 19, 2011 (with English translation).

* cited by examiner

PLASMA-GENERATING DEVICE, PLASMA SURGICAL DEVICE, USE OF A PLASMA-GENERATING DEVICE AND METHOD OF GENERATING A PLASMA

CLAIM OF PRIORITY

This application claims priority of a Swedish Patent Application No. 0501602-7 filed on Jul. 8, 2005.

FIELD OF THE INVENTION

The present invention relates to a plasma-generating device, comprising an anode, a cathode and an elongate plasma channel which extends substantially in the direction from said cathode to said anode. The plasma channel has a throttling portion which is arranged in said plasma chamber between said cathode and an outlet opening arranged in said anode. The invention also relates to a plasma surgical device, use of such a plasma surgical device in surgery and a method of generating a plasma.

BACKGROUND ART

Plasma-generating devices relate to devices which are arranged to generate a gas plasma. Such devices can be used, for instance, in surgery to stop bleeding, that is coagulation of biological tissues.

As a rule, said plasma-generating device is long and narrow. A gas plasma is suitably discharged at one end of the device and its temperature may cause coagulation of a tissue which is affected by the gas plasma.

Owing to recent developments in surgical technology, that referred to as laparoscopic (keyhole) surgery is being used more often. This implies, inter alia, a greater need for devices with small dimensions to allow accessibility without extensive surgery in surgical applications. Equipment with small dimensions are also advantageous to allow good accuracy in the handling of surgical instruments in surgery.

WO 2004/030551 (Suslov) discloses a plasma surgical device according to prior art which is intended, inter alia, to reduce bleeding in living tissue by a gas plasma. This device comprises a plasma-generating system with an anode, a cathode and a gas supply channel for supplying gas to the plasma-generating system. Moreover the plasma-generating system comprises at least one electrode which is arranged between said cathode and anode. A housing of an electrically conductive material which is connected to the anode encloses the plasma-generating system and forms the gas supply channel.

It is also desirable to provide a plasma-generating device as described above which is capable, not only of coagulation of bleeding in living tissue, but also of cutting tissue.

With the device according to WO 2004/030551, a relatively high gas flow speed of a plasma-generating gas is generally required to generate a plasma for cutting. To generate a plasma with a suitable temperature at such gas flow speeds, it is often necessary to supply a relatively high electric operating current to the device.

It is nowadays desirable to operate plasma-generating devices at low electric operating currents, since high electric operating currents are often difficult to provide in certain environments, such as medical environments. As a rule, high electric operating currents also result in extensive wiring which can get unwieldy to handle in precision work, for instance in keyhole surgery.

Alternatively, the device according to WO 2004/030551 can be formed with a substantially long plasma channel to generate a plasma with a suitable temperature at the required gas flow speeds. However, a long plasma channel can make the plasma-generating device large and unwieldy to handle in certain applications, for example medical applications, especially keyhole surgical applications.

The plasma generated should in many fields of application also be pure and have a low degree of impurities. It is also desirable that the generated plasma discharged from the plasma-generating device has a pressure and a gas volume flow that are not detrimental to, for instance, a patient who is being treated.

According to that described above, there is thus a need for improved plasma-generating devices which can be used, for instance, to cut biological tissue. There is thus a need for improved plasma-generating devices which can generate a pure plasma at lower operating currents and at lower gas volume flows.

SUMMARY OF THE INVENTION

An object of the present invention is to provide an improved plasma-generating device according to the preamble to claim 1.

Another object is to provide a plasma surgical device and use of such a plasma surgical device in the field of the surgery.

A further object is to provide a method of generating a plasma and use of such a plasma for cutting biological tissue.

According to one aspect of the invention, a plasma-generating device is provided, comprising an anode, a cathode and an elongate plasma channel which extends substantially in the direction from said cathode to said anode, which plasma channel has a throttling portion which is arranged in said plasma channel between said cathode and an outlet opening arranged in said anode. Said throttling portion of the plasma-generating device divides said plasma channel into a high pressure chamber, which is positioned on a side of the throttling portion closest to the cathode and has a first maximum cross-sectional area transverse to the longitudinal direction of the plasma channel, and a low pressure chamber which opens into said anode and has a second maximum cross-sectional area transverse to the longitudinal direction of the plasma channel, said throttling portion has a third cross-sectional area transverse to the longitudinal direction of the plasma channel which is smaller than said first maximum cross-sectional area and said second maximum cross-sectional area, at least one intermediate electrode being arranged between said cathode and said throttling portion. Preferably, the intermediate electrode can be arranged inside the high pressure chamber or form a part thereof.

This construction of the plasma-generating device allows that plasma provided in the plasma channel can be heated to a high temperature at a low operating current supplied to the plasma-generating device. In this text, by high temperature of the plasma is meant a temperature exceeding 11,000° C., preferably above 13,000° C. The provided plasma is suitably heated to a temperature between 11,000 and 20,000° C. in the high pressure chamber. In an alternative embodiment, the plasma is heated to between 13,000 and 18,000° C. In another alternative embodiment, the plasma is heated to between 14,000 and 16,000° C. Moreover, by low operating current is meant a current level below 10 Ampere. The operating current supplied to the device is suitably between 4 and 8 ampere. With these operating currents, a supplied voltage level is suitably between 50 and 150 volt.

Low operating currents are often an advantage in, for instance, surgical environments where it can be difficult to provide the necessary supply of higher current levels. As a rule, high operating current levels cause unwieldy wiring which can be difficult to handle in operations requiring great accuracy, such as surgery, in particular keyhole surgery. High operating currents can also be a safety risk for an operator and/or patient in certain environments and applications.

The invention is based on, for instance, the knowledge that a plasma which is suitable for, for instance, cutting action in biological tissue can be obtained by designing the plasma channel in a suitable manner. An advantage of the present invention is the use of a high pressure chamber and a throttling portion which allow heating of the plasma to desirable temperatures at preferred operating currents. By pressurizing the plasma upstream of the throttling portion, it is possible to increase the energy density of the plasma in the high pressure chamber. By increased energy density is meant that the energy value of the plasma per unit volume is increased. Increased energy density of the plasma in the high pressure chamber allows, in turn, that the plasma can be given a high temperature in heating by an electric arc which extends in the same direction as the plasma channel between the cathode and the anode. The increased pressure in the high pressure chamber has also been found suitable to operate the plasma-generating device at lower operating currents. Furthermore the increased pressure of the plasma in the high pressure chamber has also been found suitable to operate the plasma-generating device at lower gas volume flows of a supplied plasma-generating gas. For example, experiments have shown that pressurization of the plasma in the high pressure chamber to about 6 bar can at least allow improved efficiency by 30% of the plasma-generating device compared with prior art technique where the plasma channel is arranged without a high pressure chamber and without a throttling portion.

It has also been found that power loss in the anode can be reduced, compared with prior art plasma-generating devices, by pressurizing the plasma in a high pressure chamber.

It may also be desirable to discharge the plasma at a lower pressure than that prevailing in the high pressure chamber. For instance the increased pressure in the high pressure chamber can be detrimental to a patient in, for example, surgical operations by a plasma-generating device according to the invention. However, it has been found that a low pressure chamber which is arranged downstream of the throttling portion reduces the increased pressure of the plasma in the high pressure chamber as the plasma passes the throttling portion when flowing from the high pressure chamber to the low pressure chamber. When passing the flow portion, parts of the increased pressure of the plasma in the high pressure chamber are converted into kinetic energy and the flow speed of the plasma is thus accelerated in the low pressure chamber in relation to the flow speed in the high pressure chamber.

A further advantage of the plasma-generating device according to the invention thus is that the plasma discharged through an outlet of the plasma channel has higher kinetic energy than the plasma in the high pressure chamber. A plasma jet with such properties has been found to make it possible to use the generated plasma for, for instance, cutting living biological tissue. The kinetic energy is suitable, for example, to allow a plasma jet to penetrate an object affected by the same and thus produce a cut.

It has also been found convenient to supply to the plasma-generating device low gas volume flows in surgical applications since high gas volume flows can be detrimental to a patient who is treated with the generated plasma. With low gas volume flows of the plasma-generating gas supplied to the plasma-generating device, it has been found that there is a risk of one or more electric arcs forming between the cathode and the high pressure chamber, referred to as cascade electric arcs.

It has also been found that the risk of occurrence of such cascade electric arcs increases with a reduced cross-section of the plasma channel. Such cascade electric arcs can have a negative effect on the function of the plasma device, and the high pressure chamber can be damaged and/or degraded owing to the effect of the electric arc. There is also a risk that substances released from the high pressure chamber can contaminate the plasma, which can be detrimental, for instance, to a patient when the plasma generated in the plasma-generating device is used for surgical applications. Experiments have shown that the above problems can arise, for instance, at a gas volume flow which is less than 1.5 l/min and a cross-section of the plasma channel which is less than 1 $mm^2$.

Thus, the invention is also based on the knowledge that it has been found suitable to arrange at least one intermediate electrode in the high pressure chamber to reduce the risk that such cascade electric arcs occur. It is consequently an advantage of the plasma-generating device according to the invention that said at least one intermediate electrode allows the cross-section of the high pressure chamber to be arranged in such a manner that a desirable temperature of the electric arc, and thus a desirable temperature of the provided plasma can be achieved at the applied operating current levels stated above. It has also been found in an advantageous manner that the arrangement of an intermediate electrode in the high pressure chamber gives a reduced risk of the plasma being contaminated. An intermediate electrode arranged in the high pressure chamber also helps to heat the generated plasma in a more efficient manner. By intermediate electrode is meant in this text one or more electrodes which are arranged between the cathode and anode. It will also be appreciated that electric voltage is applied across each intermediate electrode in operation of the plasma-generating device.

Thus, the present invention provides, by the combination of at least one intermediate electrode arranged upstream of the throttling portion and a smaller cross-section of the high pressure chamber, a plasma-generating device which can be used to generate a plasma with unexpectedly low contamination levels and other good properties for surgical operation, which is useful for instance when cutting biological tissue. However, it will be noted that the plasma-generating device can also be used for other surgical applications. For instance, it is possible to generate, by variations of, for instance, operating current and/or gas flow, a plasma which can be used for, for instance, vaporization or coagulation of biological tissue. Also combinations of these applications are conceivable and in many cases advantageous in many fields of application.

It has also been found that the plasma-generating device provided according to the invention allows in a desirable manner controlled variations of a relationship between thermal energy and kinetic energy of the generated plasma. It has been found convenient to be able to use a plasma with different relationships between thermal energy and kinetic energy when treating different types of objects, such as soft and hard biological tissue. It has also been found convenient to be able to vary the relationship between thermal energy and kinetic energy depending on the blood intensity in a biological tissue that is to be treated. For instance, it has been found that in some cases it is convenient to use a plasma with a greater amount of thermal energy in connection with higher blood intensity in the tissue and a plasma with lower thermal energy in connection with lower blood intensity in the tissue. The relationship between thermal energy and kinetic energy of the generated plasma can be controlled, for example, by the pressure level established in the high pressure chamber, in which case a higher pressure in the high pressure chamber can give the plasma increased kinetic energy when being discharged from the plasma-generating device. Consequently, such variations of the relationship between thermal energy and kinetic energy of the generated plasma allow, for instance, that the combination of cutting action and coagulating action in surgical applications can be adjusted in a suitable manner for treatment of different types of biological tissue.

Suitably, said high pressure chamber is formed mainly of said at least one intermediate electrode. By letting the high pressure chamber consist wholly or partly of said at least one intermediate electrode, a high pressure chamber is obtained, which effectively heats the passing plasma. A further advantage that can be achieved by arranging the intermediate electrode as part of the high pressure chamber is that the high pressure chamber can be arranged with a suitable length without, for instance, so-called cascade electric arcs being formed between the cathode and the inner circumferential surface of the high pressure chamber. An electric arc formed between the cathode and the inner circumferential surface of the high pressure chamber can damage and/or degrade the high pressure chamber as described above.

In one embodiment of the plasma-generating device, the high pressure chamber suitably consists of a multi-electrode channel portion comprising two or more intermediate electrodes. By arranging the high pressure chamber as a multi-electrode channel portion, the high pressure chamber can be given an increased length to allow the supplied plasma to be heated to about the temperature of the electric arc. The smaller cross-section of the high pressure chamber, the longer channel has been found necessary to heat the plasma to about the temperature of the electric arc. Experiments have been made where a plurality of intermediate electrodes are used to keep down the extension of each electrode in the longitudinal direction of the plasma channel. Use of a plurality of intermediate electrodes has been found to allow a reduction of the applied electric voltage across each intermediate electrode.

It has also been found suitable to arrange a larger number of intermediate electrodes between the throttling portion and the cathode when increasing pressurization of the plasma in the high pressure chamber. In addition, it has been found that by using a larger number of intermediate electrodes when increasing the pressurization of the plasma in the high pressure chamber, it is possible to maintain substantially the same voltage level per intermediate electrode, which reduces the risk of occurrence of so-called cascade electric arcs when pressurizing the plasma in the high pressure chamber.

When a high pressure chamber with a relatively great length is used, it has been found to be a risk that the electric arc cannot be established between the cathode and the anode if each individual electrode is made too long. Instead, shorter electric arcs can be established between the cathode and the intermediate electrodes and/or between intermediate electrodes adjoining each other. It has thus been found advantageous to arrange a plurality of intermediate electrodes in the high pressure chamber and, thus, reduce the voltage applied to each intermediate electrode. Consequently it is advantageous to use a plurality of intermediate electrodes when arranging a long high pressure chamber, especially when the high pressure chamber has a small cross-sectional area. In experiments, it has been found suitable to supply to each of the intermediate electrodes a voltage which is lower than 22 volt. With preferred operating current levels as stated above, it has been found that the voltage level across the electrodes suitably is between 15 and 22 volt/mm.

In one embodiment, said high pressure chamber is arranged as a multielectrode channel portion comprising three or more intermediate electrodes.

In one embodiment of the plasma-generating device, the second maximum cross-sectional area is equal to or smaller than 0.65 $mm^2$. In one embodiment, the second maximum cross-sectional area can be arranged with a cross-section having an extension between 0.05 and 0.44 $mm^2$. In an alternative embodiment of the plasma-generating device, the cross-section can be arranged with a area between 0.13 and 0.28 $mm^2$. By arranging the channel portion of the low pressure chamber with such a cross-sectional area, it has been found possible to discharge a plasma jet with high energy concentration through an outlet of the plasma channel of the plasma-generating device. A plasma jet with high energy concentration is particularly useful in applications for cutting biological tissue. A small cross-sectional area of the generated plasma jet is also advantageous in treatments where great accuracy is required. Moreover, a low pressure chamber with such a cross-section allows the plasma to be accelerated and obtain increased kinetic energy and a reduced pressure, which is suitable, for instance, when using the plasma in surgical applications.

The third cross-sectional area of the throttling portion is suitably in a range between 0.008 and 0.12 $mm^2$. In an alternative embodiment, the third cross-sectional area of the throttling portion can be between 0.030 and 0.070 $mm^2$. By arranging the throttling portion with such a cross-section, it has been found possible to generate in a suitable manner an increased pressure of plasma in the high pressure chamber. Furthermore pressurization of the plasma in the high pressure chamber affects its energy density as described above. The pressure increase of the plasma in the high pressure chamber by the throttling portion is thus advantageous to obtain desirable heating of the plasma at suitable gas volume flows and operating current levels.

It has been found that another advantage of the selected cross-section of the throttling portion is that the pressure in the high pressure chamber can be increased to a suitable level where the plasma flowing through the throttling portion is accelerated to supersonic speed with a value equal to or greater than Mach 1. The critical pressure level required in the high pressure chamber to achieve supersonic speed of the plasma in the low pressure chamber has been found to depend on, inter alia, the cross-sectional size and geometric design of the throttling portion. It has also been found that the critical pressure to achieve supersonic speed is also affected by which kind of plasma-generating gas is used and the temperature of the plasma. It should be noted that the throttling portion always has a smaller diameter than the cross-section of both the first and the second maximum cross-sectional area in the high pressure chamber and the low pressure chamber, respectively.

Suitably the first maximum cross-sectional area of the high pressure chamber is in a range between 0.03 and 0.65 $mm^2$. Such a maximum cross-section has been found suitable for heating the plasma to the desired temperature at suitable levels for gas volume flow and operating currents.

The temperature of an electric arc which is established between the cathode and the anode has been found to be dependent on, inter alia, the dimensions of a cross-section of the high pressure chamber. A smaller cross-section of the high pressure chamber gives increased energy density of an electric arc which is established between the cathode and the anode. Consequently, the temperature of the electric arc along the centre axis of the plasma chamber is a temperature which is proportional to the relationship between a discharge current and the cross-section of the plasma channel.

In an alternative embodiment, the high pressure chamber has a cross-section between 0.05 and 0.33 $mm^2$. In another alternative embodiment, the high pressure chamber has a cross-section between 0.07 and 0.20 $mm^2$.

It may be advantageous to arrange the throttling portion in an intermediate electrode. By such an arrangement, it has been found that the risk is reduced that so-called cascade electric arcs occur between the cathode and the throttling portion. Similarly, it has also been found that the risk decreases that cascade electric arcs occur between the throttling portion and intermediate electrodes possibly adjoining the same.

It is also suitable that the low pressure chamber comprises at least one intermediate electrode. This means, inter alia, that the risk of so-called cascade electric arcs occurring between the cathode and the low pressure chamber decreases. One or more intermediate electrodes in the low pressure chamber also means that the risk decreases that cascade electric arcs occur between possibly adjoining intermediate electrodes.

In an advantageous manner, intermediate electrodes in the throttling portion and the low pressure chamber contribute to the possibility of establishing in a desirable manner an electric arc between the cathode and the anode. Moreover, for some applications it may be convenient to arrange the throttling portion between two intermediate electrodes. In an alternative embodiment of the plasma-generating device, the throttling portion can be arranged between at least two intermediate electrodes which form part of the high pressure chamber and at least two intermediate electrodes which form part of the low pressure chamber.

It has been found suitable to design the plasma-generating device in such a manner that a substantial part of the plasma channel which extends between the cathode and the anode is formed by intermediate electrodes. Such a channel is also suitable when heating of the plasma is possible along substantially the entire extent of the plasma channel.

In one embodiment of the plasma-generating device, the plasma-generating device comprises at least two intermediate electrodes, preferably at least three intermediate electrodes. In an alternative embodiment, the plasma-generating device comprises between 2 and 10 intermediate electrodes, and according to another alternative embodiment between 3 and 10 intermediate electrodes. By using such a number of intermediate electrodes, a plasma channel with a suitable length for heating a plasma at desirable levels of gas flow rate and operating current can be obtained. Moreover, said intermediate electrodes are suitably spaced from each other by insulator means. The intermediate electrodes are suitably made of copper or alloys containing copper.

In one embodiment, the first maximum cross-sectional area, the second maximum cross-sectional area and the third cross-sectional area are circular in a cross-section transverse to the longitudinal direction of the plasma channel. By forming the plasma channel with a circular cross-section, for instance manufacture will be easy and cost-effective.

In an alternative embodiment of the plasma-generating device, the cathode has a cathode tip tapering towards the anode and a part of the cathode tip extends over a partial length of a plasma chamber connected to said high pressure chamber. This plasma chamber has a fourth cross-sectional area, transverse to the longitudinal direction of said plasma channel, which fourth cross-sectional area at the end of said cathode tip which is directed to the anode is larger than said first maximum cross-sectional area. By providing the plasma-generating device with such a plasma chamber, it will be possible to provide a plasma-generating device with a reduced outer dimension. In an advantageous manner, it is possible, by using a plasma chamber, to provide a suitable space around the cathode, especially the tip of the cathode closest to the anode. A space around the tip of the cathode is suitable to reduce the risk that the high temperature of the cathode in operation damages and/or degrades material, adjacent to the cathode, of the device. In particular, the use of a plasma chamber is advantageous with long continuous times of operation.

Another advantage that is achieved by arranging a plasma chamber is that an electric arc which is intended to be established between the cathode and the anode can be safely obtained, since the plasma chamber allows the tip of the cathode to be positioned in the vicinity of the opening of the plasma channel closest to the cathode without surrounding material being damaged and/or degraded owing to the high temperature of the cathode. If the tip of the cathode is positioned at too great a distance from the opening of the plasma channel, an electric arc is often established between the cathode and surrounding structures in an unfavorable manner, which may result in incorrect operation of the device and in some cases also damage the device.

According to a second aspect of the invention, a plasma surgical device is provided, comprising a plasma-generating device as described above. Such a plasma surgical device of the type described above can suitably be used for destruction or coagulation of biological tissue, especially for cutting. Moreover, such a plasma surgical device can advantageously be used in heart or brain surgery. Alternatively, such a plasma surgical device can advantageously be used in liver, spleen or kidney surgery.

According to a third aspect of the invention, a method of generating a plasma is provided. Such a method comprises supplying, at an operating current of 4 to 10 ampere, to a plasma-generating device as described above a gas volume flow of 0.05 to 1.00 l/min of a plasma-generating gas. Such a plasma-generating gas suitably consists of an inert gas, such as argon, neon, xenon, helium etc. The method of generating a plasma in this way can be used, inter alia, to cut biological tissue.

The supplied flow of plasma-generating gas can in an alternative embodiment be between 0.10 and 0.80 l/min. In another alternative embodiment, the supplied flow of plasma-generating gas can be between 0.15 and 0.50 l/min.

According to a fourth aspect of the invention, a method of generating a plasma by a plasma-generating device is provided, comprising an anode, a cathode and a plasma channel which extends substantially in the direction from said cathode to said anode, said method comprising providing a plasma flowing from the cathode to the anode; (this direction of the plasma flow gives meaning to the terms “upstream” and “downstream” as used herein); increasing energy density of said plasma by pressurizing the plasma in a high pressure chamber which is positioned upstream of a throttling portion arranged in the plasma channel; heating said plasma by using at least one intermediate electrode which is arranged upstream of the throttling portion; and decompressing and accelerating said plasma by passing it through said throttling portion and discharging said plasma through an outlet opening of the plasma channel.

By such a method, it is possible to generate a plasma which is substantially free of contaminants and which can be heated to a suitable temperature and be given suitable kinetic energy at desirable operating currents and gas flow levels as described above.

Pressurization of the plasma in the high pressure chamber suitably comprises generating a pressure between 3 and 8 bar, preferably 5-6 bar. Such pressure levels are suitable to give the plasma an energy density which allows heating to desirable temperatures at desirable operating current levels. Such pressure levels have also been found to allow that the plasma in the vicinity of the throttling portion can be accelerated to supersonic speed.

The plasma is suitably decompressed to a pressure level which exceeds the prevailing atmospheric pressure outside the outlet opening of the plasma channel by less than 2 bar, alternatively 0.25-1 bar, and according to another alternative 0.5-1 bar. By reducing the pressure of the plasma discharged through the outlet opening of the plasma channel to such levels, the risk is reduced that the pressure of the plasma injures a patient who is surgically treated by the generated plasma jet.

By the increased pressure of the plasma in the high pressure chamber, it has been found that the plasma flowing through the plasma channel can be accelerated to supersonic speed with a value equal to or greater than Mach 1 in the vicinity of the throttling portion. The pressure that is required to achieve a speed higher than Mach 1 depends on, inter alia, the pressure of the plasma and the type of supplied plasma-generating gas. Moreover, the necessary pressure in the high pressure chamber depends on the cross-sectional area and geometric design of the throttling portion. Suitably the plasma is accelerated to a flow speed which is 1-3 times the super-sonic speed, that is a flow speed between Mach 1 and Mach 3.

The plasma is preferably heated to a temperature between 11,000 and 20,000° C., preferably 13,000 to 18,000° C., especially 14,000 to 16,000° C. Such temperature levels are suitable, for instance, in use of the generated plasma for cutting biological tissue.

To generate and provide the plasma, a plasma-generating gas can suitably be supplied to the plasma-generating device. It has been found suitable to provide such a plasma-generating gas with a flow amount between 0.05 and 1.00 l/min, preferably 0.10-0.80 l/min, especially 0.15-0.50 l/min. With such flow levels of the plasma-generating gas, it has been found possible that the generated plasma can be heated to suitable temperatures at desirable operating current levels. The above-mentioned flow levels are also suitable in use of the plasma in surgical applications since it allows a reduced risk of injuries to a patient.

When discharging the plasma through the outlet opening of the plasma channel, it is suitable to discharge the plasma as a plasma jet with a cross-section which is below 0.65 $mm^2$, preferably between 0.05 and 0.44 $mm^2$, especially 0.13-0.28 $mm^2$. Moreover the plasma-generating device is suitably supplied with an operating current between 4 and 10 ampere, preferably 4-8 ampere.

According to another aspect of the invention, the above-mentioned method of generating a plasma can be used for a method of cutting biological tissue.

BRIEF DESCRIPTION OF THE DRAWINGS

The invention will now be described in more detail with reference to the accompanying schematic drawings which by way of example illustrate currently preferred embodiments of the invention.

DESCRIPTION OF PREFERRED EMBODIMENTS

Figure 1A:
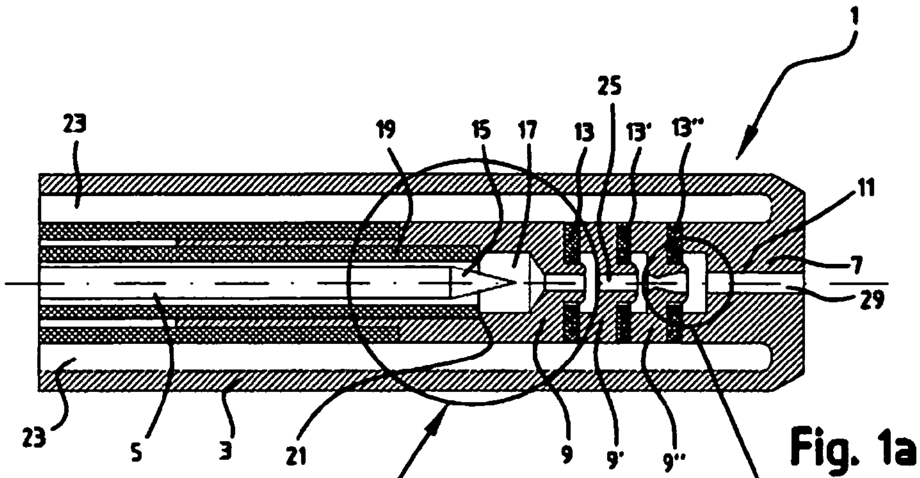
FIG. 1*a* is a cross-sectional view of an embodiment of a plasma-generating device according to the invention.

FIG. 1*a* is a cross-sectional view of an embodiment of a plasma-generating device 1 according to the invention. The cross-section in FIG. 1*a* is taken through the centre of the plasma-generating device 1 in its longitudinal direction. The device comprises an elongate end sleeve 3 which accommodates a plasma-generating system for generating plasma which is discharged at the end of the end sleeve 3. The discharge end of sleeve 3 is also referred to as the distal end of device 1. In general, the term "distal" refers to facing the discharge end of the device; the term "proximal" refers to facing the opposite direction. The terms "distal" and "proximal" can be used to describe the ends of device 1 and its elements. The generated plasma can be used, for instance, to stop bleeding in tissues, vaporize tissues, cut tissues etc.

The plasma-generating device 1 according to FIG. 1*a* comprises a cathode 5, an anode 7 and a number of electrodes 9, 9', 9" arranged between the anode and the cathode, in this text referred to as intermediate electrodes. The intermediate electrodes 9, 9', 9" are annular and form part of a plasma channel 11 which extends from a position in front of the cathode 5 and towards and through the anode 7. The inlet end of the plasma channel 11 is positioned next to the cathode 5 and the plasma channel extends through the anode 7 where its outlet opening is arranged. In the plasma channel 11 a plasma is intended to be heated so as to finally flow out through the opening of the plasma channel in the anode 7. The intermediate electrodes 9, 9', 9" are insulated and spaced from each other by an annular insulator means 13,13', 13". The shape of the intermediate electrodes 9, 9',9" and the dimensions of the plasma channel 11 can be adjusted to the desired purposes. The number of intermediate electrodes 9, 9', 9" can also be optionally varied. The embodiment shown in FIG. 1*a* is provided with three intermediate electrodes 9, 9', 9".

In the embodiment shown in FIG. 1*a*, the cathode 5 is formed as an elongate cylindrical element. Preferably, the cathode 5 is made of tungsten with optional additives, such as lanthanum. Such additives can be used, for instance, to lower the temperature occurring at the end 15 of the cathode 5.

Moreover the end 15 of the cathode 5 which is directed to the anode 7 has a tapering end portion. The tapering portion 15 suitably forms a tip positioned at the end of the cathode as shown in FIG. 1*a*. Suitably the cathode tip 15 is conical in shape. The cathode tip 15 can also be part of a cone or have alternative shapes with a geometry tapering towards the anode 7.

The other end of the cathode directed away from the anode 7 is connected to an electrical conductor to be connected to an electric energy source. The conductor is suitably surrounded by an insulator. (The conductor is not shown in FIG. 1*a*.)

A plasma chamber 17 is connected to the inlet end of the plasma channel 11 and has a cross-sectional area, transverse to the longitudinal direction of the plasma channel 11, which exceeds the cross-sectional area of the plasma channel 11 at the inlet end thereof. The plasma chamber 17 as shown in FIG. 1*a* is circular in cross-section, transverse to the longitudinal direction of the plasma channel 11, and has an extent $L_{ch}$ in the longitudinal direction of the plasma channel 11 which corresponds to approximately the diameter $D_{ch}$ of the plasma chamber 17. The plasma chamber 17 and the plasma channel 11 are substantially concentrically arranged relative to each other. The cathode 5 extends into the plasma chamber 17 at least half the length $L_{ch}$ thereof and the cathode 5 is arranged substantially concentrically with the plasma chamber 17. The plasma chamber 17 consists of a recess integrated in the first intermediate electrode 9 which is closest to the cathode 5.

FIG. 1*a* also shows an insulator element 19 which extends along and around a substantial portion of the cathode 5. The insulator element 19 is suitably formed as an elongate cylindrical sleeve and the cathode 5 is partly positioned in a circular hole extending through the tubular insulator element 19. The cathode 5 is arranged substantially in the centre of the through hole of the insulator element 19. Moreover the inner diameter of the insulator element 19 is slightly greater than the outer diameter of the cathode 5, thus forming a distance between the outer circumferential surface of the cathode 5 and the inner surface of the circular hole of the insulator element 19.

Preferably the insulator element 19 is made of a temperature-resistant material, such as ceramic material, temperature-resistant plastic material or the like. The insulator element 19 intends to protect adjoining parts of the plasma-generating device from high temperatures which can occur, for instance, around the cathode 5, in particular around the tip 15 of the cathode.

The insulator element 19 and the cathode 5 are arranged relative to each other so that the end 15 of the cathode 5 directed to the anode projects beyond an end face 21, which is directed to the anode 7, of the insulator element 19. In the embodiment shown in FIG. 1*a*, approximately half the tapering tip 15 of the cathode 5 extends beyond the end face 21 of the insulator element 19.

A gas supply part (not shown in FIG. 1*a*) is connected to the plasma-generating part. The gas supplied to the plasma-generating device 1 advantageously consists of the same type of gases that are used as plasma-generating gas in prior art instruments, for instance inert gases, such as argon, neon, xenon, helium etc. The plasma-generating gas is allowed to flow through the gas supply part and into the space arranged between the cathode 5 and the insulator element 19. Consequently the plasma-generating gas flows along the cathode 5 inside the insulator element 19 towards the anode 7. As the plasma-generating gas passes the end 21 of the insulator element 19 which is positioned closest to the anode 7, the gas is passed into the plasma chamber 17.

The plasma-generating device 1 further comprises one or more coolant channels 23 which extend into the elongate end sleeve 3. The coolant channels 23 are suitably partly made in one piece with a housing (not shown) which is connected to the end sleeve 3. The end sleeve 3 and the housing can, for instance, be interconnected by a threaded joint, but also other connecting methods, such as welding, soldering etc, are conceivable. Moreover the end sleeve suitably has an outer dimension which is less than 10 mm, preferably less than 5 mm. At least a housing portion positioned at the end sleeve suitably has an outer shape and dimension which substantially correspond to the outer shape and dimension of the end sleeve. In the embodiment of the plasma-generating device shown in FIG. 1*a*, the end sleeve is circular in cross-section transversely to the longitudinal direction of the plasma channel 11.

In one embodiment, the plasma-generating device 1 comprises two additional channels 23, one constituting an inlet channel and the other constituting an outlet channel for a coolant. The inlet channel and the outlet channel communicate with each other to allow the coolant to pass through the end sleeve 3 of the plasma-generating device 1. It is also possible to provide the plasma-generating device 1 with more than two cooling channels, which are used to supply or discharge coolant. Preferably water is used as coolant, although other types of fluids are conceivable. The cooling channels are arranged so that the coolant is supplied to the end sleeve 3 and flows between the intermediate electrodes 9, 9', 9'' and the inner wall of the end sleeve 3. The interior of the end sleeve 3 constitutes the area that connects the at least two additional channels to each other.

The intermediate electrodes 9, 9', 9'' are arranged inside the end sleeve 3 of the plasma-generating device 1 and are positioned substantially concentrically with the end sleeve 3. The intermediate electrodes 9, 9', 9'' have an outer diameter which in relation to the inner diameter of the end sleeve 3 forms an space between the outer surface of the intermediate electrodes and the inner wall of the end sleeve 3. It is in this space the coolant supplied from the additional channels 23 is allowed to flow between the intermediate electrodes 9, 9', 9'' and the end sleeve 3.

The additional channels 23 can be different in number and be given different cross-sections. It is also possible to use all, or some, of the additional channels 23 for other purposes. For example, three additional channels 23 can be arranged where, for instance, two are used for supply and discharge of coolant and one for sucking liquids, or the like, from an area of surgery etc.

In the embodiment shown in FIG. 1*a*, three intermediate electrodes 9, 9', 9'' are spaced apart by insulator means 13, 13', 13'' which are arranged between the cathode 5 and the anode 7. However, it will be appreciated that the number of electrodes 9, 9', 9'' can be optionally selected according to any desired purpose. The intermediate electrodes adjoining each other and the insulator means arranged between them are suitably press-fitted to each other.

The intermediate electrode 9'' which is positioned furthest away from the cathode 5 is in contact with an annular insulator means 13'' which is arranged against the anode 7.

The anode 7 is connected to the elongate end sleeve 3. In the embodiment shown in FIG. 1*a*, the anode 7 and the end sleeve 3 are formed integrally with each other. In alternative embodiments, the anode 7 can be formed as a separate element which is joined to the end sleeve 3 by a threaded joint between the anode and the end sleeve, by welding or by soldering. The connection between the anode 7 and the end sleeve 3 is suitably such as to provide electrical contact between them.

The plasma-generating device 1 shown in FIG. 1*a* has a plasma channel 11 which comprises a high pressure chamber 25, a throttling portion 27 and a low pressure chamber 29. The throttling portion 27 is positioned between the high pressure chamber 25 and the low pressure chamber 29. Thus by high pressure chamber 25 is meant in this text a part of the plasma chamber 11 which is positioned upstream of the throttling portion 27 in the flow direction of the plasma from the cathode 5 to the anode 7. By low pressure chamber 29 is meant that part of the plasma channel 11 which is positioned downstream of the throttling portion 27.

Figure 1C:
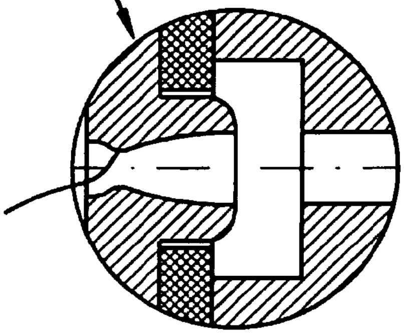
FIG. 1*c* is a partial enlargement of a throttling portion which is arranged in a plasma channel of the plasma-generating device in FIG. 1*a;*

The throttling portion 27 shown in FIG. 1*a* constitutes the smallest cross-section of the plasma channel 11. Consequently the cross-section of the throttling portion 27 is smaller than the maximum cross-section of the high pressure chamber 25 and the maximum cross-section of the low pressure chamber 29, transversely to the longitudinal direction of the plasma channel. As shown in FIGS. 1*a* and 1*c*, the throttling portion is preferably a supersonic or a de Laval nozzle.

The throttling portion 27 causes the pressure in the high pressure chamber 25 to be increased in relation to the pressure in the low pressure chamber 29. When the plasma flows through the throttling portion 27, the flow speed of the plasma is accelerated and the pressure of the plasma drops. Consequently a plasma discharged through the opening of the plasma channel 11 in the anode 7 has higher kinetic energy and a lower pressure than the plasma in the high pressure chamber 25. According to the plasma-generating device shown in FIG. 1*a*, the opening of the plasma channel 11 in the anode 7 has the same cross-sectional area as the maximum cross-sectional area of the low pressure chamber 29.

The plasma channel 11 in the embodiment shown in FIG. 1*a* is preferably formed so that the plasma channel 11 gradually tapers to a smallest cross-section of the throttling portion so as then to gradually increase in cross-section again. This form of the plasma channel 11 in the vicinity of the throttling portion 27 reduces, for instance, turbulence in the plasma. This is advantageous since turbulence may otherwise reduce the flow speed of the plasma.

In the partial enlargement shown in FIG. 1*c* the plasma channel 11 has a converging channel portion upstream of the smallest cross-sectional area of the throttling portion 27, seen in the flow direction of the plasma. Moreover the plasma channel 11 has a diverging channel portion downstream of the throttling portion 27. In the embodiment shown in FIG. 1*c*, the diverging part of the plasma channel 11 has a shorter extent in the longitudinal direction of the plasma channel 11 than the converging part.

With the design of the plasma channel 11 in the vicinity of the throttling portion 27, in the embodiment of the plasma-generating device shown in FIG. 1*c*, it has been found possible to accelerate the plasma in the throttling portion 27 to supersonic speed with a value which is equal to or greater than Mach 1.

The plasma channel 11 shown in FIG. 1*a* is circular in cross-section. Suitably the high pressure chamber has a maximum diameter between 0.20 and 0.90 mm, preferably 0.25-0.65 mm, in particular 0.30-0.50 mm. Moreover the low pressure chamber suitably has a maximum diameter between 0.20 and 0.90 mm, preferably 0.25-0.75 mm, in particular 0.40-0.60 mm. The throttling portion suitably has a minimum diameter between 0.10 and 0.40 mm, preferably 0.20-0.30 mm.

The exemplary embodiment of the plasma-generating device 1 shown in FIG. 1*a* has a high pressure chamber 25 with a diameter of 0.4 mm. The low pressure chamber 29 has a diameter of 0.50 mm and the throttling portion 27 has a diameter of 0.27 mm in the embodiment shown in FIG. 1*a*.

In the embodiment of the plasma-generating device shown in FIG. 1*a*, the throttling portion 27 is positioned substantially in the centre of the extent of the plasma channel in the longitudinal direction. However, it has been found possible to vary the relationship between kinetic energy and thermal energy of the plasma depending on the location of the throttling portion 27 in the plasma channel 11.

Figure 2:
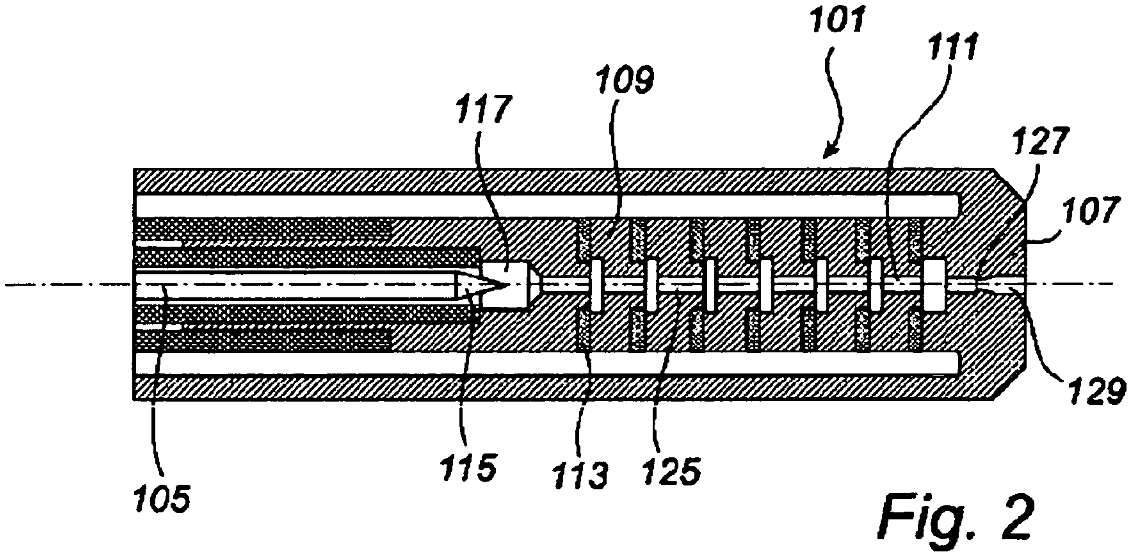
FIG. 2 illustrates an alternative embodiment of a plasma-generating device.

FIG. 2 is a cross-sectional view of an alternative embodiment of the plasma-generating device 101. In the embodiment shown in FIG. 2, the throttling portion 127 is positioned in the anode 107 in the vicinity of the outlet opening of the plasma channel 111. By arranging the throttling portion 127 far downstream in the longitudinal direction of the plasma channel 111, for instance in the anode 107 or in the vicinity of the anode 107, a plasma can be obtained at the opening of the plasma channel 111 which has a higher amount of kinetic energy compared with the plasma-generating device 1 shown in FIG. 1*a*. It has been found that a certain type of tissue, for instance soft tissue such as liver tissue, can be cut more easily with a plasma having a higher amount of kinetic energy. For example, it has been found suitable to generate a plasma which consists of approximately half thermal energy and half kinetic energy for such cutting.

Moreover the alternative embodiment of the plasma-generating device 101 in FIG. 2 comprises seven intermediate electrodes 109. However, it will be appreciated that the embodiment of the plasma-generating device 101 in FIG. 2 can optionally be arranged with more or fewer than seven intermediate electrodes 109.

Figure 3:
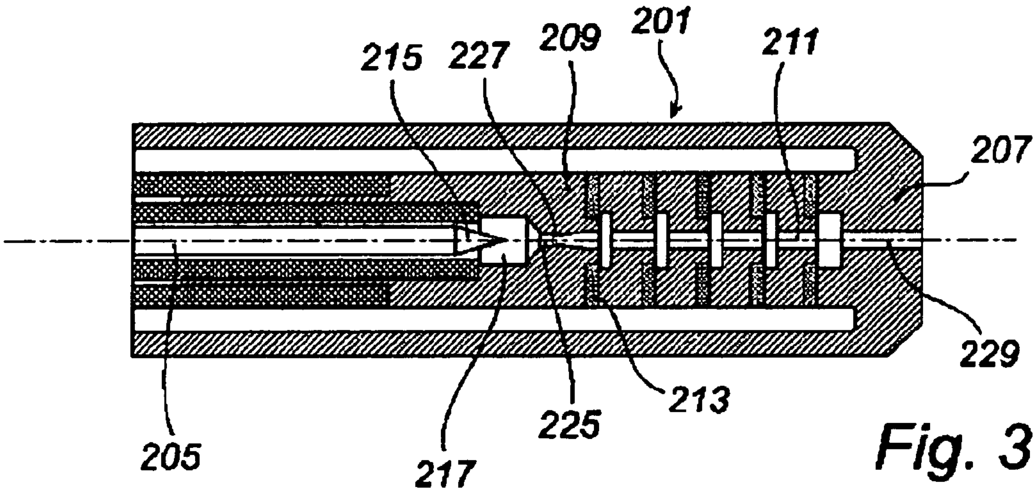
FIG. 3 illustrates another alternative embodiment of a plasma-generating device.

FIG. 3 shows another alternative embodiment of the plasma-generating device 201. In the embodiment shown in FIG. 3, the throttling portion 227 is placed in the first intermediate electrode 209 closest to the cathode 205. By arranging the throttling portion 227 considerably far upstream in the extent of the plasma channel 211, a plasma can be obtained, which has a lower amount of kinetic energy when being discharged through the outlet opening of the plasma channel 211 compared with the embodiments in FIGS. 1*a* and 2. It has been found that, for instance, certain hard tissue, such as bone, can be cut more easily with a plasma having a higher amount of thermal energy and a lower amount of kinetic energy. For example, it has been found convenient to generate a plasma which consists of approximately 80-90% thermal energy and 10-20% kinetic energy for such cutting.

Moreover the alternative embodiment of the plasma-generating device 201 in FIG. 2 comprises five intermediate electrodes 209. However, it will be appreciated that the embodiment of the plasma-generating device 201 in FIG. 2 can optionally be arranged with more or fewer than five intermediate electrodes 209.

It will appreciated that the throttling portion 27; 127; 227 can be arranged in an optional position in the plasma channel 11; 111; 211 depending on desirable properties of the generated plasma. Moreover it will be appreciated that the embodiments shown in FIGS. 2-3, in addition to the differences described above, can be arranged in a way similar to that described for the embodiment in FIGS. 1*a*-1*c*.

Figure 4:
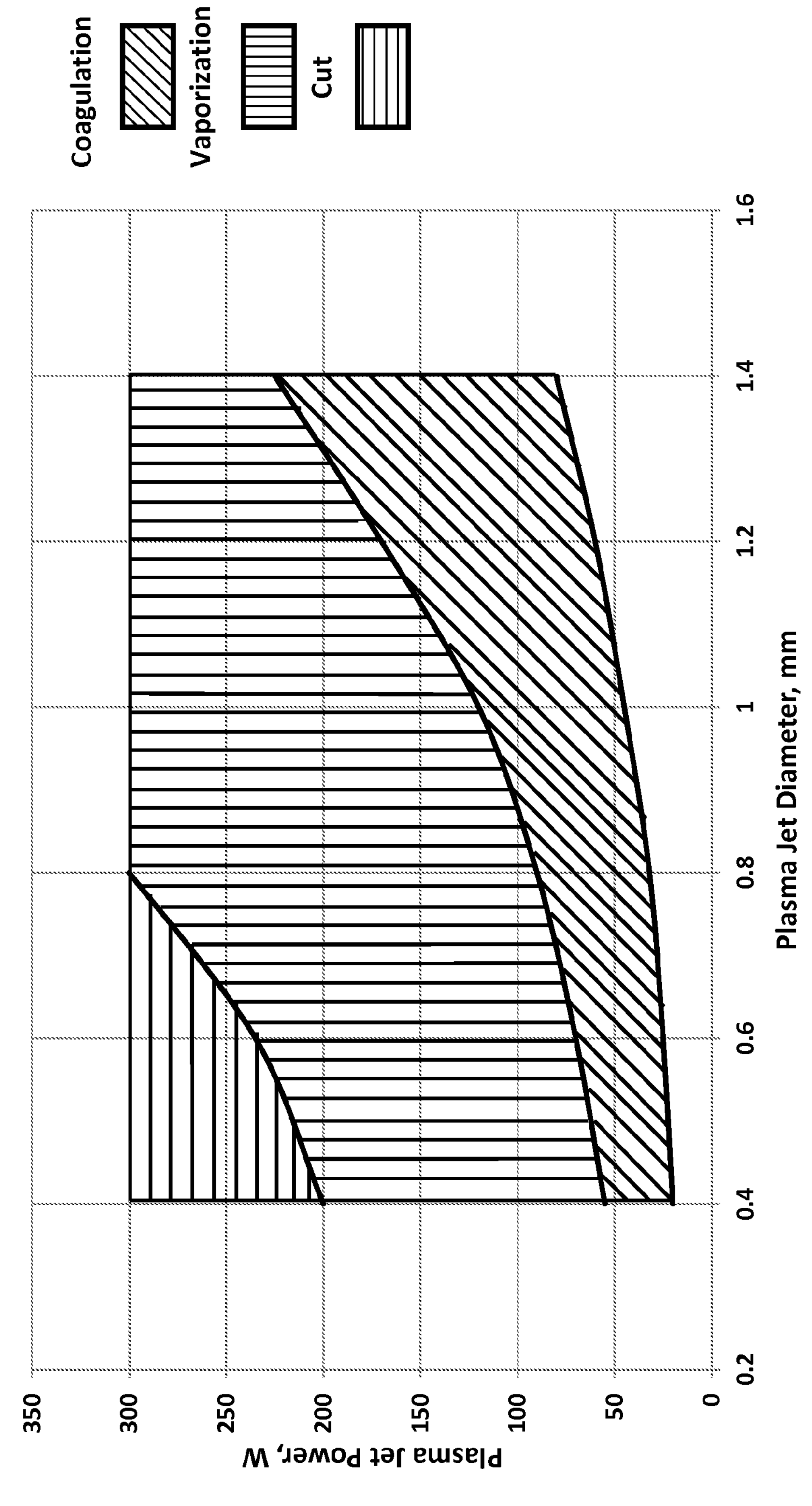
FIG. 4 shows in a diagram, by way of example, suitable power levels to affect biological tissue in different ways.

FIG. 4 shows by way of example suitable power levels to achieve different effects on a biological tissue. FIG. 4 shows how these power levels relate to different diameters of a plasma jet which is discharged through the plasma channel 1; 111; 211 of a plasma-generating device 1; 101; 201 as described above. To achieve different effects, such as coagulation, vaporization and cutting, on a living tissue, the power levels shown in FIG. 4 are suitable. These different types of effect can be achieved at different power levels depending on the diameter of the plasma jet. To keep the necessary operating currents down, it has thus been found convenient to reduce the diameter of the plasma channel 11; 111; 211 of the plasma-generating device, and consequently a plasma jet generated by the device, as shown in FIG. 4.

Figure 5:
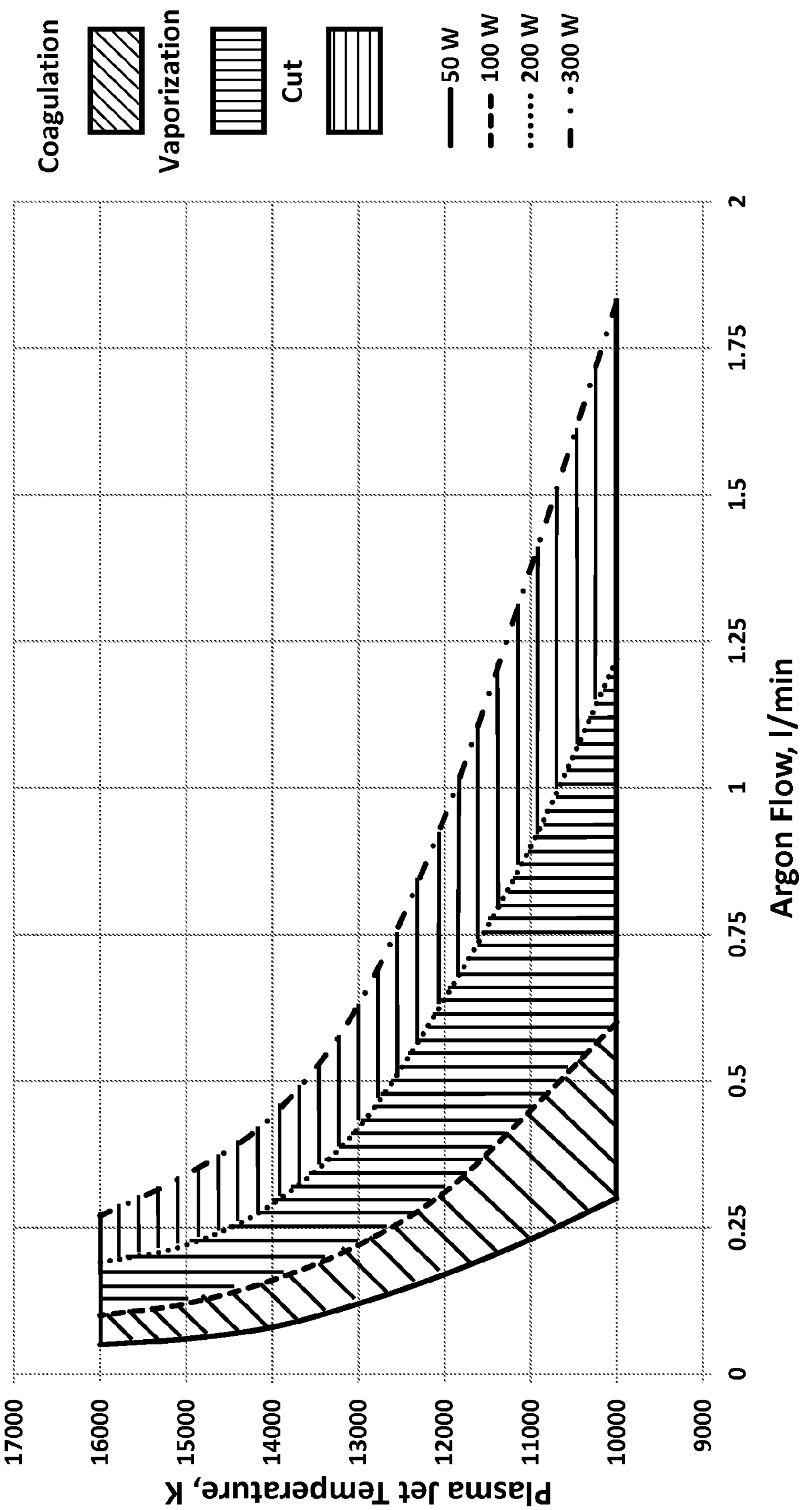
FIG. 5 shows in a diagram, at different operating power levels, the relationship between the temperature of a plasma jet and the gas volume flow of provided plasma-generating gas for a plasma-generating device.

FIG. 5 shows the relationship between the temperature of the plasma jet and the volume flow of the provided plasma-generating gas, for instance argon, for a plasma-generating device 1; 101; 201 as described above. To achieve the desirable effect, such as coagulation, vaporization or cutting, it has been found convenient to use a certain supplied gas volume flow at different power levels as shown in FIG. 5. To generate a plasma with a desirable temperature, as described above in this text, at suitable power levels, it has been found desirable to provide a low gas volume flow of the plasma-generating gas. To keep the necessary operating currents down, it has thus been found convenient to reduce the gas volume flow of the supplied plasma-generating gas to the plasma-generating device 1; 101; 201. A high gas volume flow can also be detrimental to, for instance, a patient who is being treated and should thus suitably be kept low.

Consequently, it has been found that a plasma-generating device 1; 101; 201 in the embodiment shown in FIGS. 1*a*-3 makes it possible to generate a plasma with these properties. This has, in turn, been found advantageous to provide a plasma-generating device 1; 101; 201 which can be used for cutting, for instance, living biological tissue at suitable operating currents and gas volume flows.

Suitable geometric relationships between the parts included in the plasma-generating device 1; 101; 201 will be described below with reference to FIGS. 1*a*-1*b*. It will be noted that the dimensions stated below constitute only exemplary embodiments of the plasma-generating device 1; 101; 201 and can be varied depending on the field of application and the desired properties. It will also be noted that the examples described in FIGS. 1*a*-*b* can also be applied to the embodiments in FIGS. 2-3.

The inner diameter $d_i$ of the insulator element 19 is only slightly greater than the outer diameter $d_c$ of the cathode 5. In one embodiment, the difference in cross-section, in a common cross-section, between the cathode 5 and the insulator element 19 is suitably equal to or greater than a cross-section of the inlet of plasma channel next to the cathode 5.

Figure 1B:
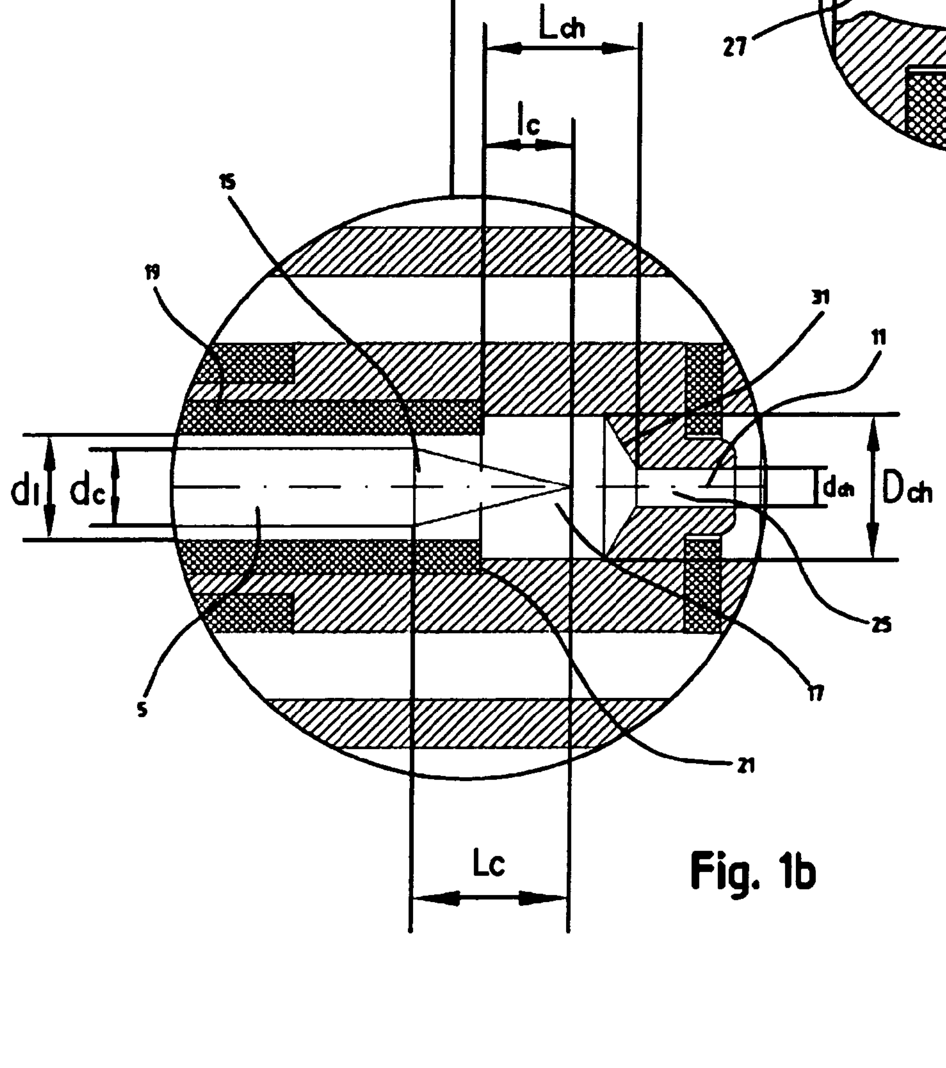
FIG. 1*b* is partial enlargement of the embodiment in FIG. 1*a;*

In the embodiment shown in FIG. 1*b*, the outer diameter $d_c$ of the cathode 5 is about 0.50 mm and the inner diameter $d_i$ of the insulator element 19 is about 0.80 mm.

In one embodiment, the cathode 5 is arranged so that a partial length of the cathode tip 15 projects beyond a boundary surface 21 of the insulator element 19. In FIG. 1*b*, the tip 15 of the cathode 5 is positioned so that approximately half the length $L_c$ of the tip 15 projects beyond the boundary surface 21 of the insulator element 19. In the embodiment shown in FIG. 1*b*, this projection $l_c$ corresponds to approximately the diameter $d_c$ of the cathode 5.

The total length $L_c$ of the cathode tip 15 is suitably greater than 1.5 times the diameter $d_c$ of the cathode 5 at the base of the cathode tip 15. Preferably, the total length $L_c$ of the cathode tip 15 is about 1.5-3 times the diameter $d_c$ of the cathode 5 at the base of the cathode tip 15. In the embodiment shown in FIG. 1*b*, the length $L_c$ of the cathode tip 15 corresponds to approximately 2 times the diameter $d_c$ of the cathode 5 at the base of the cathode tip 15.

In one embodiment, the diameter $d_c$ of the cathode 5 is about 0.3-0.6 mm at the base of the cathode tip 15. In the embodiment shown in FIG. 1*b*, the diameter $d_c$ of the cathode 5 is about 0.50 mm at the base of the cathode tip 15. Preferably, the cathode has substantially the same diameter $d_c$ between the base of the cathode tip 15 and the end, opposite to the cathode tip 15, of the cathode 5. However, it will be appreciated that it is possible to vary this diameter $d_c$ along the extent of the cathode 5.

In one embodiment, the plasma chamber 17 has a diameter $D_{ch}$ which corresponds to approximately 2-2.5 times the diameter $d_c$ of the cathode 5 at the base of the cathode tip 15. In the embodiment shown in FIG. 1*b*, the plasma chamber 17 has a diameter $D_{ch}$ which corresponds to approximately 2 times the diameter $d_c$ of the cathode 5.

The extent $L_{ch}$ of the plasma chamber 17 in the longitudinal direction of the plasma-generating device 1 corresponds to approximately 2-2.5 times the diameter $d_c$ of the cathode 5 at the base of the cathode tip 15. In the embodiment shown in FIG. 1*b*, the length $L_{ch}$ of the plasma chamber 17 corresponds to approximately the diameter $D_{ch}$ of the plasma chamber 17.

In one embodiment, the tip 15 of the cathode 5 extends over half the length $L_{ch}$ of the plasma chamber 17 or over more than half said length. In an alternative embodiment, the tip 15 of the cathode 5 extends over ½ to ⅔ of the length $L_{ch}$ of the plasma chamber 17. In the embodiment shown in FIG. 1*b*, the cathode tip 15 extends at least half the length $L_{ch}$ of the plasma chamber 17.

The cathode 5 extending into the plasma chamber 17 is in the embodiment shown in FIG. 1*b* positioned at a distance from the end of the plasma chamber 17 closest to the anode 7 which corresponds to approximately the diameter $d_c$ of the cathode 5 at the base thereof.

In the embodiment shown in FIG. 1*b*, the plasma chamber 17 is in fluid communication with the high pressure chamber 25 of the plasma channel 11. The high pressure chamber 25 suitably has a diameter $d_{ch}$ which is approximately 0.2-0.5 mm. In the embodiment shown in FIG. 1*b*, the diameter $d_{ch}$ of the high pressure chamber 25 is about 0.40 mm. However, it will be appreciated that the diameter $d_{ch}$ of the high pressure chamber 25 can be varied in different ways along the extent of the high pressure chamber 25 to provide different desirable properties.

A transition portion 31 is arranged between the plasma chamber 17 and the high pressure chamber 25, constituting a tapering transition, in the direction from the cathode 5 to the anode 7, between the diameter $D_{ch}$ of the plasma chamber 17 and the diameter $d_{ch}$ of the high pressure chamber 25. The transition portion 31 can be designed in a number of alternative ways. In the embodiment shown in FIG. 1*b*, the transition portion 31 is designed as a bevelled edge which forms a transition between the inner diameter $D_{ch}$ of the plasma chamber 17 and the inner diameter $d_{ch}$ of the high pressure chamber 25. However, it will be appreciated that the plasma chamber 17 and the high pressure chamber 25 can be arranged in direct contact with each other, without a transition portion 31 arranged between the two. The use of a transition portion 31 as shown in FIG. 1*b* results in advantageous heat extraction for cooling of structures adjacent to the plasma chamber 17 and the high pressure chamber 25.

The plasma-generating device 1 can advantageously be provided as a part of a disposable instrument. For instance, a complete device with the plasma-generating device 1, outer shell, tubes, coupling terminals etc. can be sold as a disposable instrument. Alternatively, only the plasma-generating device 1 can be disposable and connected to multiple-use devices.

Other embodiments and variants are conceivable with-in the scope of the present invention. For instance, the number and shape of the electrodes 9, 9', 9" can be varied according to which type of plasma-generating gas is used and the desired properties of the generated plasma.

In use, the plasma-generating gas, such as argon, is supplied through the gas supply part to the space between the cathode 5 and the insulator element 19 as described above. The supplied plasma-generating gas is passed on through the plasma chamber 17 and the plasma channel 11 to be discharged through the opening of the plasma channel 11 in the anode 7. Having established the gas supply, a voltage system is switched on, which initiates a discharge process in the plasma channel 11 and establishes an electric arc between the cathode 5 and the anode 7. Before establishing the electric arc, it is convenient to supply coolant to the plasma-generating device 1 through the coolant channel 23, as described above. Having established the electric arc, a gas plasma is generated in the plasma chamber 17 and, during heating, passed on through the plasma channel 111 towards the opening thereof in the anode 7.

A suitable operating current for the plasma-generating devices 1, 101, 201 in FIGS. 1-3 is 4-10 ampere, preferably 4-8 ampere. The operating voltage of the plasma-generating device 1, 101, 201 is, inter alia, dependent on the number of intermediate electrodes and the length of the intermediate electrodes. A relatively small diameter of the plasma channel enables relatively low energy consumption and relatively low operating current when using the plasma-generating device 1, 101, 201.

In the electric arc established between the cathode and the anode, a temperature T prevails in the centre thereof along the centre axis of the plasma channel and is proportional to the relationship between the discharge current I and the diameter $d_{ch}$ of the plasma channel ($T=k*I/d_{ch}$). To provide a high temperature of the plasma, for instance 11,000 to 20,000° C., at the outlet of the plasma channel in the anode, at a relatively low current level, the cross-section of the plasma channel, and thus the cross-section of the electric arc heating the gas, should be small. With a small cross-section of the electric arc, the electric field strength in the plasma channel has a high value.

The different embodiments of a plasma-generating device according to FIGS. 1*a*-3 can be used, not only for cutting living biological tissue, but also for coagulation and/or vaporization. With a simple movement of his hand, an operator can suitably switch the plasma-generating device between coagulation, vaporization and coagulation.

What is claimed:

1. A plasma surgical device comprising:

an anode, positioned at an outermost distal end of the device, a cathode;

an electrical insulator sleeve surrounding a substantial portion of the cathode, wherein there is a gap formed by an inside surface of the insulator sleeve and an outside surface of the cathode, the gap being capable of passing a plasma-generating gas; and one or more intermediate electrodes electrically insulated from each other and from the anode, one or more of the intermediate electrodes forming a plasma channel having an inlet at a location between the cathode and the anode, the plasma channel extending longitudinally through a hole in the anode and having an outlet opening at a distal end of the anode, the plasma channel having a throttling portion, the throttling portion dividing the plasma channel into (1) a high pressure chamber positioned upstream of the throttling portion formed by two or more intermediate electrodes and having a first maximum transverse cross-sectional area, and (2) a low pressure chamber positioned downstream of the throttling portion and having a second maximum transverse cross-sectional area, the throttling portion having a third transverse cross-sectional area, which is smaller than the first maximum transverse cross-sectional area and the second maximum transverse cross-sectional area.

2. The plasma surgical device of claim 1, wherein the throttling portion is a supersonic nozzle.

3. The plasma surgical device of claim 2, wherein the second maximum transverse cross-sectional area is less than or equal to 0.65 $mm^2$.

4. The plasma surgical device of claim 3, wherein the third transverse cross-sectional area is between 0.008 and 0.12 $mm^2$.

5. The plasma surgical of claim 4, wherein the first maximum transverse cross-sectional area is between 0.03 and 0.65 $mm^2$.

6. The plasma surgical device of claim 2, wherein the throttling portion is arranged longitudinally between two of the intermediate electrodes.

7. The plasma surgical device of claim 6, wherein the throttling portion is arranged longitudinally between (a) at least two of the intermediate electrodes forming a part of the high pressure chamber and (b) at least two of the intermediate electrodes forming a part of the low pressure chamber.

8. The plasma surgical device of claim 2, wherein a distal end of the cathode has a tapered portion that partially projects beyond a distal end of the insulator sleeve.

9. The plasma surgical device of claim 8, wherein the throttling portion is a de Laval nozzle.

10. The plasma surgical device of claim 1, wherein the high pressure chamber is formed by three or more of the intermediate electrodes.

11. The plasma surgical device of claim 1, wherein the part of the plasma channel being formed by the intermediate electrodes is formed by two or more intermediate electrodes.

12. The plasma surgical device of claim 11, wherein the part of the plasma channel being formed by the intermediate electrodes is formed by 3-10 intermediate electrodes.

13. The plasma surgical device of claim 1, wherein the high pressure chamber has a cylindrical portion and the low pressure chamber has a cylindrical portion.

14. The plasma surgical device of claim 1, wherein one of the intermediate electrodes forms a plasma chamber connected to the inlet of the plasma channel, wherein a distal end of the cathode extends longitudinally into the plasma chamber to some distance away from the inlet of the plasma channel, wherein the plasma chamber has a transverse cross-sectional area greater than the first maximum cross-sectional area.

15. The plasma surgical device of claim 14, wherein the throttling portion is formed by a single of the intermediate electrodes that is distinct from the intermediate electrode forming the plasma chamber.

16. A method of using the plasma surgical device of claim 1 for cutting biological tissue comprising a step of discharging plasma from the outlet of the plasma channel on the biological tissue.

17. The method of claim 16, wherein the biological tissue is one of liver, spleen, heart, brain, or kidney.

18. The method of claim 16, wherein the discharged plasma is suitable for cutting biological tissue.

19. The plasma surgical device of claim 1 adapted for use in laparoscopic surgery.

20. A method of generating plasma comprising a step of supplying to the plasma surgical device of claim 1 the plasma-generating gas at a rate of 0.05 to 1.00 l/min, and establishing an electric arc of 4-10 Amperes between the cathode and the anode.

21. The method of 20, wherein the plasma-generating gas is an inert gas.

22. The method of claim 21, wherein the plasma-generating gas is argon.

23. The method of claim 20, wherein the generated plasma creates a static pressure between 3 and 8 bar in the high pressure chamber and a static pressure of up to 3 bar in the low pressure chamber.

24. The method of claim 23, wherein the electric arc is capable of heating the generated plasma in the high pressure chamber to a temperature between 11,000 and 20,000°C.

25. The plasma surgical device of claim 1 having an outer cross-sectional width of 10 mm or less.

* * * * *